United States Patent
Jalde et al.

(10) Patent No.: US 6,739,336 B1
(45) Date of Patent: May 25, 2004

(54) ARRANGEMENT AND METHOD FOR FEEDBACK CONTROL OF A GAS FLOW IN A BREATHING ASSIST APPARATUS

(75) Inventors: Fredrik Jalde, Stockholm (SE); Anders Steiner, Stockholm (SE)

(73) Assignee: Maquet Critical Care AB, Solna (SE)

(*) Notice: Subject to any disclaimer, the term of this patent is extended or adjusted under 35 U.S.C. 154(b) by 439 days.

(21) Appl. No.: 09/666,386

(22) Filed: Sep. 20, 2000

(30) Foreign Application Priority Data

Sep. 24, 1999 (SE) ................................. 9903467

(51) Int. Cl.$^7$ ............................................ A61M 16/00
(52) U.S. Cl. .......................... 128/204.21; 128/204.23
(58) Field of Search ........................ 128/200.24, 202.22, 128/204.21, 204.23

(56) References Cited

U.S. PATENT DOCUMENTS

| | | | |
|---|---|---|---|
| 4,421,113 A | | 12/1983 | Gedeon et al. ......... 128/204.23 |
| 4,957,107 A | * | 9/1990 | Sipin ..................... 128/204.21 |
| 4,971,049 A | * | 11/1990 | Rotariu et al. ......... 128/204.21 |
| 5,253,640 A | * | 10/1993 | Falb et al. ............. 128/200.24 |
| 5,271,389 A | | 12/1993 | Isaza et al. ............ 128/204.21 |
| 5,303,698 A | | 4/1994 | Tobia et al. ............ 128/204.21 |
| 5,671,730 A | * | 9/1997 | Ollila .................... 128/204.21 |
| 5,694,926 A | * | 12/1997 | DeVries et al. ........ 128/204.21 |
| 5,803,066 A | * | 9/1998 | Rapoport et al. ...... 128/204.21 |
| 6,135,967 A | * | 10/2000 | Fiorenza et al. ....... 128/200.24 |
| 6,398,739 B1 | * | 6/2002 | Sullivan et al. ........ 128/204.23 |

FOREIGN PATENT DOCUMENTS

| EP | 0 560 490 A1 | 9/1993 |
|---|---|---|
| EP | 0 671 181 A1 | 9/1995 |

* cited by examiner

Primary Examiner—Aaron J. Lewis
(74) Attorney, Agent, or Firm—Schiff Hardin LLP

(57) ABSTRACT

A feedback controller for regulating respiratory gas in a mechanical breathing aid system has a comparator means for periodically generating, in a current breathing cycle, an error signal representing the difference between a value of a gas parameter measured for gas within the system and a target value of the gas parameter, and a control signal generator for processing the error signal in accordance with a control function to generate a control signal usable in the regulation of the respiratory gas. The controller has a variable value integral gain stage which provides an input to an integrator element. An adaption unit determines, for the current breathing cycle an extreme value of the periodically generated error signal and varies the value of the integral gain used in the integral gain stage for a next breathing cycle dependent on a rate of change of the value of the extreme error signal with value of the integral gain.

10 Claims, 4 Drawing Sheets

ARRANGEMENT AND METHOD FOR FEEDBACK CONTROL OF A GAS FLOW IN A BREATHING ASSIST APPARATUS

BACKGROUND OF THE INVENTION

1. Field of the Invention

The present invention relates to an apparatus and method for the feedback control of respiratory gas flow within a mechanical breathing assist apparatus and in particular to an apparatus and method for the adaptive feedback control of the gas flow.

2. Description of the Prior Art

Feedback controllers are used within a mechanical breathing assist apparatus, such as a ventilator system, to adjust gas flow rates based on a measurement of a system gas parameter, for example gas pressure, rise time, or flow rate, in order to achieve and maintain the value of that variable at or within an operating range of a target value. These controllers are usually operably connected to a flow control regulator, such as a solenoid valve, to provide a control signal used to adjust the opening of the valve. How the adjustment is made to reach the target value depends not only on the measured value of the system flow parameter that is fed back to the controller, but also on additional parameters known as control parameters. These control parameters directly affect the performance and stability of the controller and their optimal values may change with time as system properties, such as compliance and resistance, vary. A mechanical breathing assist apparatus is particularly problematical to control in this manner since its pneumatic system includes (or is connected in use to) a patient's respiratory system, including lungs, the compliance and resistance of which can change unpredictably with time and with patient.

In order to overcome this problem it is known to provide controllers having control parameters which automatically vary or "adapt" with changes in properties of the ventilator system. One such controller which provides an adaptation for a next breath that is based on the analysis of gas delivery in previous breaths is disclosed in U.S. Pat. No. 5,271,389. This controller has a comparator for periodically generating in a current breathing cycle, an error signal representing the difference between a value of a gas parameter measured for gas within the system and a target value of the gas parameter, a control signal generator for processing the error signal in accordance with a control function having a variable value control parameter to generate a control signal usable in the regulation of the respiratory gas, and adaption means for varying the value of the variable value control parameter responsive to the error signal. The adaption means operates by summing the error signal in a particular period with all past error signals for the corresponding period of past breaths to provide a cumulative error signal which is used to vary the control parameter for the same period of the next breath. Thus the correction will "improve" as the error values from more breaths are added to the cumulative signal.

SUMMARY OF THE INVENTION

It is an object of the present invention to provide an adaptive feedback control of gas flow within a mechanical breathing aid system in which the adaption is made on a breath-by-breath basis without the need to rely on a cumulative error signal.

The above object is achieved in accordance with the principles of the present invention in a feedback controller for regulating respiratory gas flow in a mechanical breathing assist apparatus, having a comparator which periodically generates, in a current breathing cycle, an error signal which represents a difference between a value of a gas parameter that was measured for gas within the system, and a target value for this gas parameter, a control signal generator which processes the error signal using a control function having a control parameter with a variable value, to generate a control signal used to regulate the respiratory gas, and an adaptation unit for varying the value of the control parameter dependent on the error signal, by determining, for the current breathing cycle, an extreme value of the periodically generated error signal and by varying the value of the control parameter for a next breathing cycle dependent on the rate of change of the extreme value of the error signal relative to the value of the control parameter in the current breathing cycle.

By providing for the adaptive variation of a variable control parameter for a subsequent breathing cycle which is based on the change of an extreme error signal value (that is a maximum or a minimum value depending on how the error signal is derived and which phase of the breathing cycle is being controlled) with the value of the control parameter, then disturbances in the breathing assist apparatus system are automatically compensated, based on the past performance of the system and typically based on the performance of the system over consecutive breathing cycles, without the need to establish a cumulative error signal.

Preferably an integral gain control parameter is varied assuming a linear relationship between an extreme pressure error signal and the value of the integral gain parameter. In a feedback controller, such as a PID or PI controller in which respectively a "proportional-integral-derivative" or a "proportional-irtegral" control function is implemented, the integral gain parameter that is found to be highly sensitive to disturbances in the pneumatic system such as changes in lung resistance and compliance.

DESCRIPTION OF THE PREFERRED EMBODIMENTS

Figure 1:
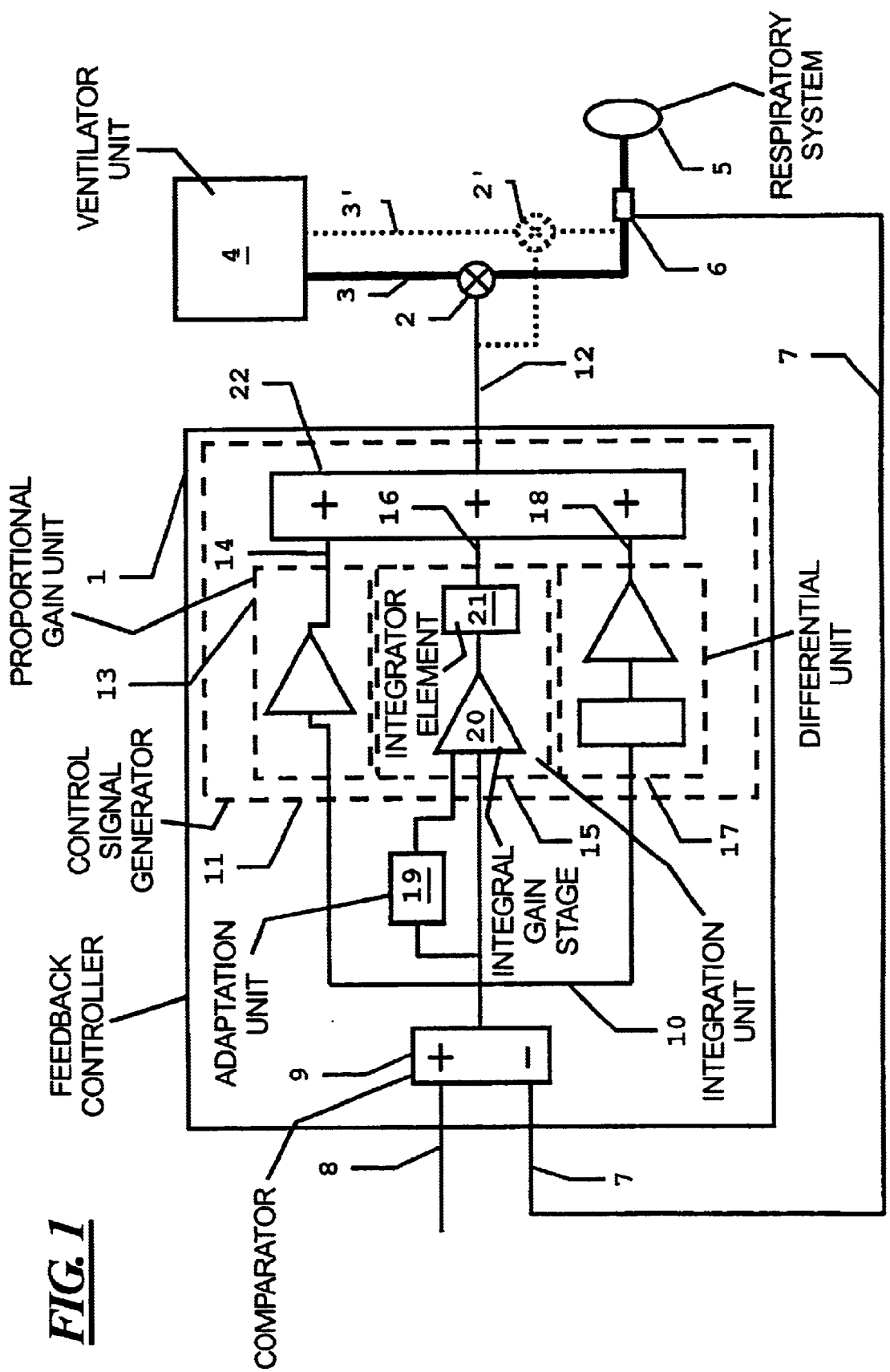
FIG. 1 is a schematic diagram of a section of a ventilator system including a feedback controller according to the present invention.

Considering now FIG. 1, a feedback controller 1 is shown which is adapted to control one or both of an inspiration gas flow control valve 2 and an expiration gas flow control valve 2'. These valves 2, 2' are respectively disposed in an inspiration gas flow path 3 and an expiration gas flow path 3' of a respiration gas which flows between a ventilator unit 4 and a patient's respiratory system 5. A sensor unit 6 is also provided within the flow path 3 (and also the flow path 3') to measure a gas pressure, and its output is supplied periodically (typically at a sample frequency of several kHz) as an input 7 to the controller 1. Also provided as an input to the controller 1 is a signal 8 that is representative of a desired or target gas pressure.

The feedback controller 1 includes a comparator 9 which receives the input target 8 and actual flow parameter signals 7 for a particular breathing cycle and periodically generates an error value signal 10 representative of their difference; and a control signal generator 11 which receives the error value signal and uses it to establish a control signal 12 for periodically controlling one or both of the valves 2, 2' during the breathing cycle.

The control signal generator 11 includes a proportional gain unit 13 which receives the error value signal 10 and amplifies it by a predetermined amount to produce a proportional signal 14 component of the control signal 12; an integration unit 15 for producing an integral signal 16 component of the control signal 12; and a differential unit 17 for producing a differential signal 18 component of the control signal 12. The feedback controller 1 of the present embodiment is thus of a type commonly referred to as a PID controller.

The feedback controller 1 also includes an adaption unit 19 which receives the error signal 10, and first determines a maximum value of the error signals 10 that have been generated periodically during a predetermined portion of the breathing cycle and then, dependent on the so determined maximum value, determines a gain parameter for use in the next breathing cycle. This gain parameter is based on a calculation within the adaption unit 19 of the rate of change of the maximum value relative to the value of the gain parameter from previous breathing cycles that is stored within a memory (not shown) of the adaption unit 19, as will be discussed in greater detail below.

The integrator unit 15 includes an integral gain stage 20 which receives the periodic error signal 10 and amplifies it by an amount dependent on the value of the gain parameter passed from the adaption unit 19 before passing it to an integrator element 21 where it is integrated to provide the integral signal component 16 of the control signal 12. A summing element 22 sums the proportional signal component 14, the integral signal component 16 and the differential signal component 18 and emits the sum as an output for use as the control signal 12.

The following discussion assumes, for the present embodiment, that the controller 1 is adapted to control the inspiration valve 2 during an inspiration phase of a breathing cycle. In controlling the flow valve 2 it is desirable to provide a small initial overshoot (O) of the target pressure since this will result in a shorter rise time.

However the overshoot (O) should not be too large since this may cause discomfort and even injury to a patient's respiratory system 5. The overshoot (O) is therefore intended to be controlled to lie within upper (a) and lower (b) limits. The maximum value of the error signal 10 then is a measure of this overshoot (O) and may be a negative value, which in this case would represent an undershoot. By arranging for the integral gain (I), used in the integral gain stage 20, to adapt its value depending on the size of this overshoot (O), the feedback controller 1 will be responsive to the type of lung 5 connected to the flow path 3 as well as to changes within the flow path 3 itself. This is because the magnitude of the integral gain (I) is highly dependent on the mechanical resistance and compliance of the pneumatic system 3,5.

Now, assuming a linear relationship between the overshoot (O) and the integral gain value (I) which is used in the integration unit 15, the desired integral gain value (I3) required to provide a satisfactory overshoot (O3) in a next breath is given by $$I3=I2+[(I1-I2)\times(O3-O2)/(O1-O2)] \quad (1)$$

wherein I1 and O1 are respectively the gain value and the overshoot associated with a previous breath (preferably the immediately preceding breath); and I2 and O2 are respectively the gain value and the overshoot associated with the current breath.

If the value of the desired overshoot (O3) for the next breath is selected to lie midway between the limits a,b of an acceptable overshoot, then equation (1) may be re-written as $$I3=I2+[(I1-I2)\times(((a+b)/2)-O2)/(O1-O2)] \quad (2)$$

With $(O1-O2)/(I1-I2)$ written as $dO/dI$, the rate of change of overshoot with gain value, then equation (2) can be expressed as $$I3=I2+[((a+b)/2)/(dO/dI)] \quad (3)$$

Figure 2:
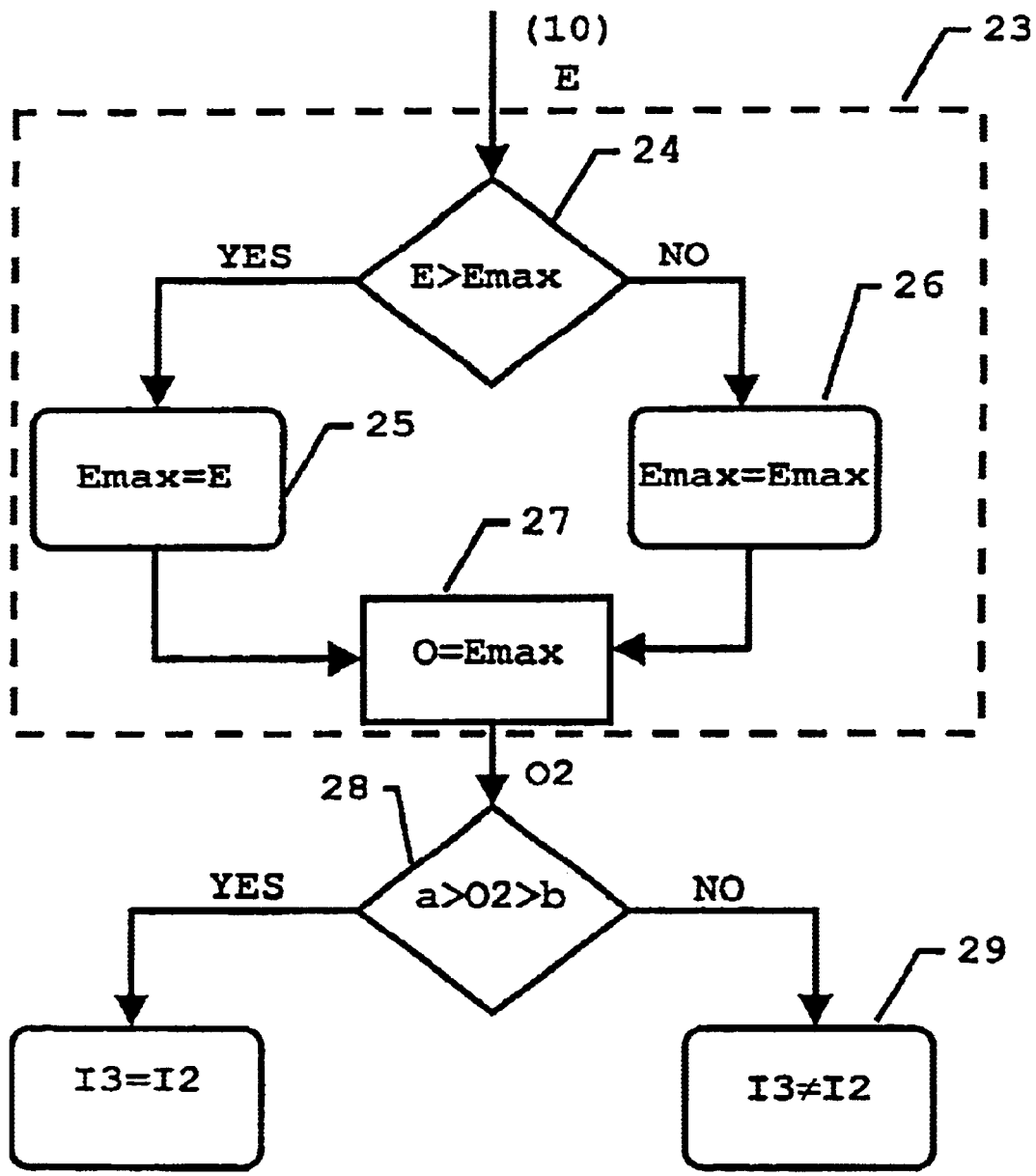
FIG. 2 shows a flow chart of the operation of an adaption means of the feedback controller of FIG. 1.
Figure 3:
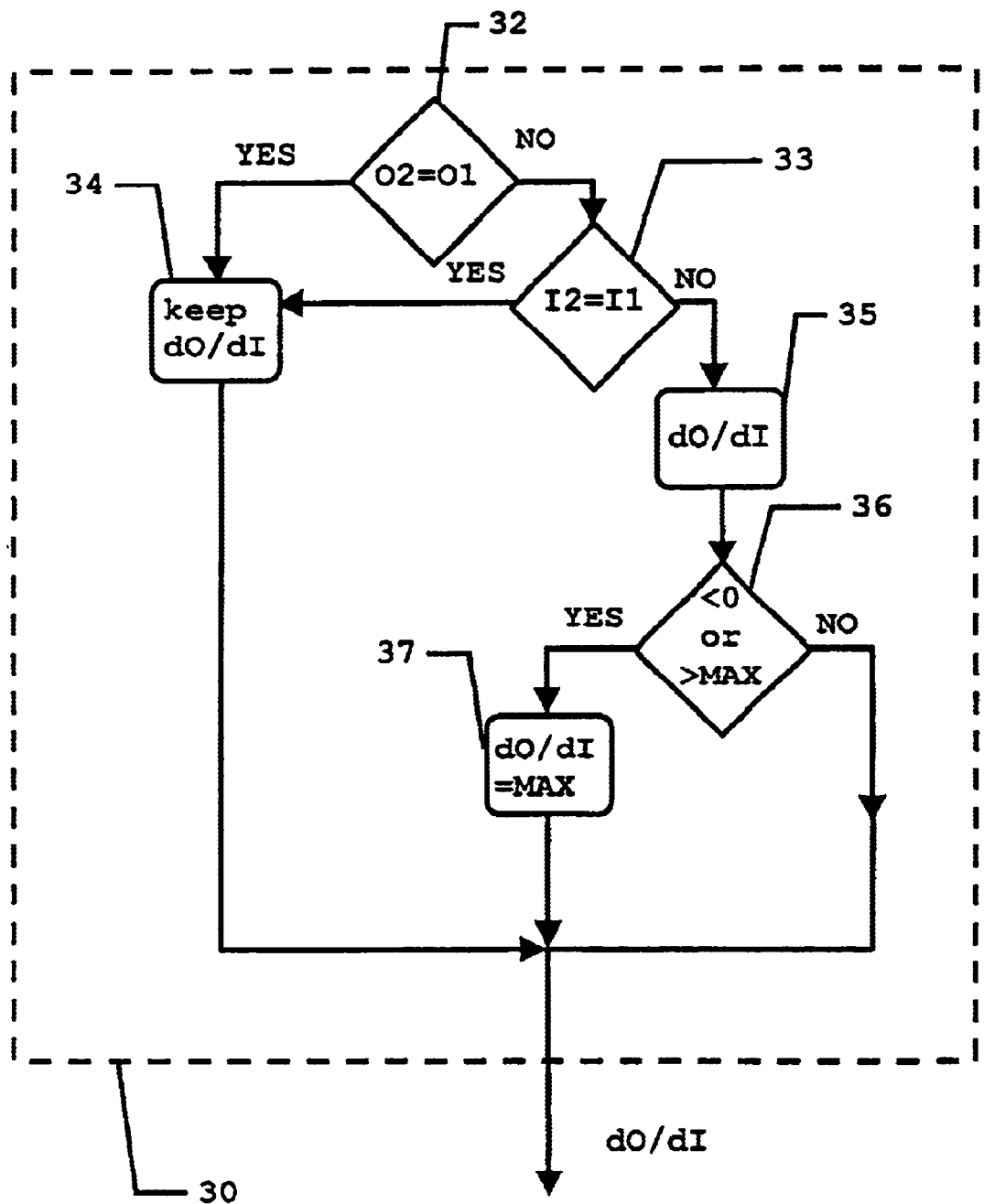
FIG. 3 shows a flow chart for the calculation of the rate of change of I gain by the adaption means the operation of which is shown in FIG. 2.
Figure 4:
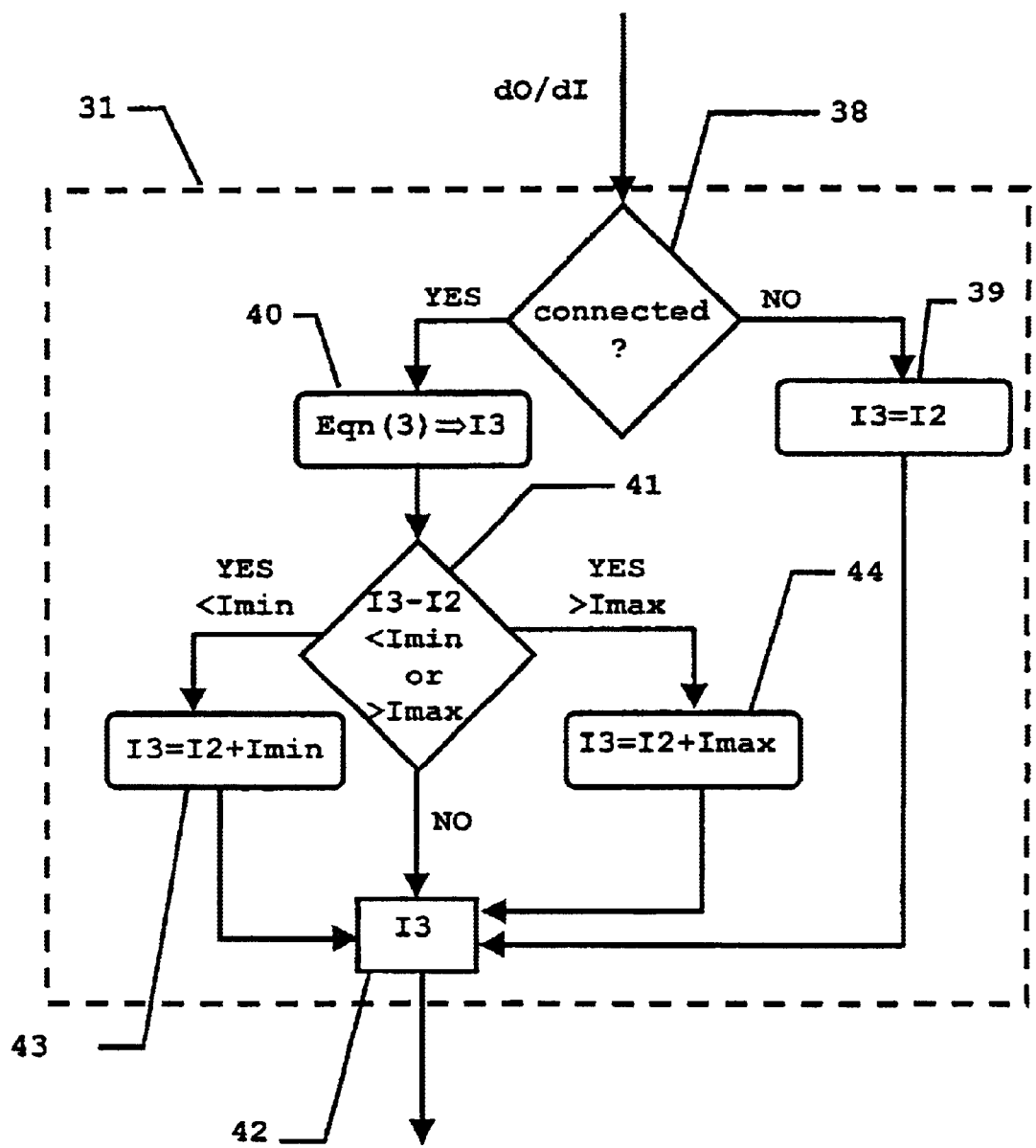
FIG. 4 shows a flow chart for the calculation of I gain from the rate of change calculated according to the steps of FIG. 3.

Considering now FIG. 2, FIG. 3 and FIG. 4, flow charts for the operation of the adaption means 19 are shown. The first step 23 is to calculate within a specified time period from the beginning of an inspiration phase (which is typically of the order of 100 ms for neonates and 200 ms for adults) a maximum error signal, Emax, from periodically determined error signals 10 entered during this period as an error value E. This first step 23 includes a step 24 of comparing the currently input error value E with a stored value of Emax obtained during the specified period of the current breathing cycle and either replacing (step 25) the current value of Emax with the value E of the current error signal 10 or maintaining (step 26) the stored value of Emax. After the specified period, step 27 is performed making the last stored value of Emax the value of the overshoot (O2) for the current breath. In step 28 a decision is made as to whether a new value of the integral gain should be provided as the integral gain control parameter (I3) for the next breath. If the overshoot (O2) for the present breath falls outside the predetermined limits a,b, then a new value of integral gain control parameter (I3) is determined (step 29) for use in the next breath.

The step 29 of determining the gain control parameter (I3) includes a step 30 (FIG. 3) for calculating a rate of change of overshoot with integral gain control value (dO/dI) and a step 31 (FIG. 4) wherein, based on this value, the gain control parameter (I3) is calculated for use in the integral gain stage 20 of the feedback controller 1. The step 29 of gain control determination may need to be carried out iteratively until the overshoot (O) lies within the desired upper (a) and lower (b) limits since the linear relationship is only an approximation which becomes better for consecutive breaths.

In calculating the value dO/dI (step 30 of FIG. 3) it is first determined (step 32) whether the overshoot O2, associated with the current breath, is equal to that overshoot O1, associated with a previous, preferably immediately preceding, breath. If it is, or if it is not but it is determined (step 33) that the current gain control value 12 and the previous one I1 are the same, then dO/dI maintains its previous value (step 34) when the new gain value I3 is calculated (step 31). If the overshoots O2 and O1, and the integral gain control parameters I2 and I1, differ, then the value (dO/dI) is calculated (step 35). If this value lies within limits (step 36) that are selected to discriminate against inaccuracies in the measurements, which have been made, then this value is used in the calculation of the new I gain (step 31) I3. If the value dO/dI lies outside these limits then dO/dI is set to MAX (step 37) and this value used in calculating the new integral gain (step 31) I3. The lower limit used at step 36 is here chosen as 0 since a change in I gain is expected to provide a change in overshoot and the upper limit as a maximum allowable value MAX above which an unexpectedly change indicative of a spike or "glitch" is considered to have occurred.

The step 31 (FIG. 4) of calculating the gain value I3 includes a first step (step 38) of determining whether a patient is connected to the ventilator 4.

If a patient has been disconnected for some reason, for example for the removal of secretion from a patient's throat, then the new gain value I3 is set to the current gain value I2 (step 39). This is done in order to prevent a "runaway" gain value I3 being set, which may lead to a patient being exposed to dangerous pressure levels when reconnected. Otherwise a new gain value 13 is calculated (step 40) using equation (3). If the difference between this new gain value I3 and the current gain value I2 lies within preset limits (Imin and Imax in step 41), selected to ensure that a pressure which is not too extreme can be delivered to the patient, then the value of I3 that was calculated at step 40 is provided for output (step 42) for use within the integral gain stage 20 of the integration unit 15. If this difference, calculated at step 41 is less than the lower limit, Imin, then I3 is set to I2−Imin (step 43). If this difference, calculated at step 39, is larger than the upper limit, Imax, then I3 is set to I2+Imax (step 44). The new value of the integral gain control parameter I3 is then supplied as an output at step 42 for use within the feedback controller 1 in the regulation of the valve 2 in the inspiration phase of the next breathing cycle.

It will be appreciated that expiration pressure within the gas flow path 3' may be controlled, for example to maintain a pre-determined PEEP level, in a manner similar to that described above with respect to inspiration pressure regulation. In this case the expiration valve 2' is controlled by the feedback controller 1, modified to provide adaptive regulation of the expiration pressure. The adaption unit 19 will operate principally according to the flow charts shown in FIGS. 2 and 3 but using different limits and a different time period which an extreme error value E will be determined. Typically this time period begins upon detection that an error signal (defined as PEEP value —pressure measured at sensor 6) is larger than 0.5 cm $H_2O$ and that the derivative of the error signal is negative. The time period ends a predetermined time, typically in the range of 100–200 ms, after it begins.

Although modifications and changes may be suggested by those skilled in the art, it is the intention of the inventors to embody within the patent warranted hereon all changes and modifications as reasonably and properly come within the scope of their contribution to the art.

We claim as our invention:

1. A feedback controller for regulating respiratory gas in a mechanical breathing assist apparatus, said feedback controller comprising:
    a measurement unit which measures a value of a gas parameter associated with respiratory gas;
    a comparator supplied with said value of said gas parameter, and with a target value for said gas parameter, said comparator periodically generating, in a current breathing cycle, an error signal representing a difference between said value of said gas parameter and said target value of said gas parameter;
    a control signal generator supplied with said error signal for processing said error signal using a control function having a control parameter with a variable value, to generate a control signal for regulating said respiratory gas; and
    an adaptation unit connected to said control signal generator for varying said value of said control parameter dependent on said error signal, by determining, for said current breathing cycle, an extreme value of said error signal and for varying said value of said control parameter for a next breathing cycle dependent on a rate of change of said extreme error signal relative to said value of said control parameter in said current breathing cycle.

2. A feedback controller as claimed in claim 1 wherein said adaptation unit determines said rate of change for consecutive breathing cycles.

3. A feedback controller as claimed in claim 1 wherein said adaptation unit varies said value of said control parameter conditional on said extreme value of said error signal being outside of a predetermined range.

4. A feedback controller as claimed in claim 1 wherein said measurement unit measures a gas pressure value as said gas parameter, and wherein said comparator is supplied with a target gas pressure value and generates said error signal as a difference between the measured gas pressure value and the target gas pressure value.

5. A feedback controller as claimed in claim 4 wherein said control signal generator regulates said respiratory gas dependent on said control parameter being within limits to inhibit said measured gas pressure value from being less than said target gas pressure value.

6. A feedback controller as claimed in claim 4 wherein said control signal generator comprises an integration unit having an integral gain stage connected to said adaptation unit to receive an output from said adaptation unit as a variable integral gain value.

7. A feedback controller as claimed in claim 6 wherein said adaptation unit varies said integral gain value dependent on a linear relationship between said extreme value of said error signal and said integral gain value.

8. A method for regulating gas in a ventilator, comprising the steps of:
    periodically determining a current error value in a current breathing cycle as a difference between a value of a parameter measured for gas within a breathing assist system and a predetermined target value;
    periodically executing a control function dependent on said error value for regulating said gas, said control function having a control parameter with a variable value, and varying said value of said control parameter dependent on said current error value and an error value generated in a previous breathing cycle, by determining, in said current breathing cycle, an extreme value of said current error signal and determining a rate of change of said extreme value relative to said control parameter and calculating said control parameter dependent on said rate of change for a next breathing cycle.

9. A method as claimed in claim 8 wherein the step of executing said control function comprises executing an integral control function having an integral gain value as said control parameter.

10. A method as claimed in claim 9 wherein the step of periodically determining said current error value comprises measuring an actual gas pressure of said gas and wherein the step of calculating the control parameter comprises calculating said control parameter dependent on a linear relationship between said extreme value of said error signal and a value of said integral gain.

* * * * *